United States Patent
Young et al.

(10) Patent No.: US 6,228,608 B1
(45) Date of Patent: May 8, 2001

(54) RECOMBINANT FIV GLYCOPROTEIN 160 AND P24 GAG PROTEIN

(75) Inventors: Eli Young, Sharon; Deborah Davis, Sterling; James Storey, Linwood; Gerald Beltz, Lexington, all of MA (US)

(73) Assignee: Aquila Biopharmaceuticals, Inc., Framingham, MA (US)

( * ) Notice: Subject to any disclaimer, the term of this patent is extended or adjusted under 35 U.S.C. 154(b) by 0 days.

(21) Appl. No.: 07/661,370

(22) Filed: Feb. 28, 1991

(51) Int. Cl.⁷ .................. C07K 14/155; C12N 15/49; C12N 15/70; A61K 39/21
(52) U.S. Cl. ............ 435/69.1; 435/252.3; 435/252.33; 435/320.1; 435/471; 530/350; 530/395; 530/826; 514/2; 424/819; 536/23.72
(58) Field of Search .................. 435/69.1, 172.3, 435/69.3, 252.3, 252.33, 320.1; 536/27, 23.2

(56) References Cited

U.S. PATENT DOCUMENTS

| | | | |
|---|---|---|---|
| 4,753,873 | 6/1988 | Beltz et al. | 435/5 |
| 4,772,547 | 9/1988 | Heimer et al. | 435/5 |
| 4,784,941 | * 11/1988 | Watanabe et al. | 435/5 |
| 4,808,536 | 2/1989 | Chang et al. | 435/5 |
| 4,925,784 | 5/1990 | Crowl et al. | 435/5 |
| 5,118,602 | * 6/1992 | Pederson et al. | 435/5 |
| 5,177,014 | * 1/1993 | O'Connor et al. | 435/188 |
| 5,275,813 | * 1/1994 | Yamamoto et al. | 424/208.1 |
| 5,510,106 | * 4/1996 | Yamamoto et al. | 424/207.1 |
| 5,591,572 | * 1/1997 | Kemp et al. | 435/5 |
| 5,637,753 | * 8/1991 | Pedersen et al. | 435/235.1 |
| 5,648,209 | * 7/1997 | Avrameas et al. | 435/5 |

FOREIGN PATENT DOCUMENTS

| | | | |
|---|---|---|---|
| 0219106 | * 4/1987 | (EP) | 435/172.3 |
| 0231914 | 8/1987 | (EP) | |
| 0255190 | 2/1988 | (EP) | |
| 0279688 | 8/1988 | (EP) | |
| 0351248 | * 1/1990 | (EP) | 435/5 |
| 87-06260 | * 10/1987 | (WO) | 435/172.3 |
| 90-13573 | * 11/1990 | (WO) | 530/350 |

OTHER PUBLICATIONS

Colasanti, J., et al., 1987, *Molecular and General Genetics*, 209:382–390.*
Teeuwsen, V.J.P., et al., 1990, *Aids Research and Human Retroviruses*, 6(3): 381–392.*
Starcich, N.R., et al, 1986, *Cell*, 45:637–648.*
Pauletti, P., et al., 1985, *Analytical Biochemistry*, 151: 540–546.*
Modrow, S., et al., 1987, *Journal of Virology*, 61(2): 570–578.*
W Chang, N.T., et al., 1985, *Science*, 228: 93–96.*
Gargo, C., et al., 1988, *Virology*, 164: 531–536.*
Sternberg, M.J.E., et al., 1987, *FEBS Letters*, 218(2):231–237.*
Alizon, M., et al., 1986, *Cell*, 46: 63–74.*
Haffar, O., et al., 1990, *Journal of Virology* 64(6): 2653–2659.*
Olmsted, R.A., et al., in *Vaccines 90*, Brown, F., Ed., Cold Spring Harbor Laboratory Press, 1990, at pp. 364–374.*
Willey, R.L. et al., 1986, *Proceedings of the National Academy of Sciences, USA*, 83: 5038–5042.*

(List continued on next page.)

Primary Examiner—Ponnathapu Achutamurthy
Assistant Examiner—William W. Moore
(74) Attorney, Agent, or Firm—Hale and Dorr LLP

(57) ABSTRACT

Feline immunodeficiency virus antigens from gp160 envelope protein, gp120 envelope protein and p24 gag protein, useful for the diagnosis, treatment, and prevention of FIV. The invention may also be used to purify FIV.

18 Claims, 3 Drawing Sheets

OTHER PUBLICATIONS

Sparger, E. L., 1990, "Feline Immunodeficiency Virus: Punrogenesis and Regulation of Viral Gene Expression." (abstract) *Dissertation Abstracts International,* 51(11): 5150-B–5151-B.*

Steinman, R., et al., 1990, *Journal of General Virology,* 71: 701–706.*

Rossi, P., et al., 1989 *Proceedings of the National Academy of Sciences USA,* 86: 8055–8085.*

Brodeur, N.R., et al., 1991, *Journal of General Virology,* 72: 51–58.*

Nanberg, J.H., et al., 1990, Journal of Cellular Biochemistry, Suppl. 140, p.140(abstract).*

Bugge, T.H., et al., 1990, Journal of Virology, 64(9):4123–4129.*

Chiodi, F., et al., 1987, Aids Research and Human Retroviruses, 3(2) : 165–176.*

Robinson, W. E., et al., 1990, Proceedings of the National Academy of Sciences, USA, vol. 87, "Human monoclonal antibodies to the human immunodeficiency virus type 1 (HIV–1) transmembrane glycoprotein gp41 enhance HIV–1 infection in vivo", pp. 3185–3189.*

Freed, E. O., et al., 1990, Proceedings of the National Academy of Sciences, USA, vol. 87, "Characterization of the fusion domain of the human immunodeficiency virus type 1 glycoprotein gp41", pp. 4650–4654.*

Battles et al., *Journal of Cellular Biochemistry 4:Supplement 14D,* p. 130, Abstract L 302 (1990).

Hu et al. *Virology 179;*321–329 (1990).

Janvier et al., Journal of Virology 64:4258–4263 (1990).

Poss et al., *Journal of Virology 64(9)* : 4338–4345 (1990).

Morikawa et al., *Virology 186:*389–397 (1992).

Poss et al., *Journal of Virology 63 (1)* :189–195 (1989).

Vzorov et al., *AIDS Research and Human Retroviruses 7 (1)* : 29–36 (1991).

Zwart et al., *Virology 181*:481–489 (1991).

Olmsted, Robert A., et al., *Proc. Natl. Acad. Sci.* 86:2448–2452 (1989).

Talbott, Randy L., et al. *Proc. Nat. Acad. Sci.* 86:5743–5747 (1989).

Dow, Steven W., et al., *Journal of Acquired Immune Deficiency Syndromes 3*:658–668 (1990).

* cited by examiner

Primer 1: position 8178 to 8204 (5'amplimer)
5'-GGGCCCCGGATCCGGTAACACAATACCACCAAGTTCTGGC-3'

Primer 2: Reverse compliment of position 8551 to 8578 (3'amplimer)
5'-CCCGGGGGATCCCCTTCCCACTTTTGTAATTGTTGTATCCC-3'

Figure 1: The sequences of the PCR primers. The underlined regions indicate BamHI restriction sites.

Purified FIV recombinant proteins.
Lane 1 are molecular weight markers.
Lane 2 is the FIV 1.2 envelope protein.
Lane 3 is the p24 gag protein and
Lane 4 is the purified recombinant
FIV 0.4 diagnostic protein.

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 30 base pairs
      (B) TYPE: nucleic acid
      (C) STRANDEDNESS: both
      (D) TOPOLOGY: linear (ii) MOLECULE TYPE: DNA (xi) SEQUENCE DESCRIPTION: SEQ ID NO:1:

CCGGGGATCC GGAGTACCAC AATATGTAGC      30

(2) INFORMATION FOR SEQ ID NO:2:

(i) SEQUENCE CHARACTERISTICS:
      (A) LENGTH: 30 base pairs
      (B) TYPE: nucleic acid
      (C) STRANDEDNESS: both
      (D) TOPOLOGY: linear (ii) MOLECULE TYPE: DNA (xi) SEQUENCE DESCRIPTION: SEQ ID NO:2:

GGCCGGATCC CTTCTAGGGT ACTTTCTGGC      30

(2) INFORMATION FOR SEQ ID NO:3:

(i) SEQUENCE CHARACTERISTICS:
      (A) LENGTH: 30 base pairs
      (B) TYPE: nucleic acid
      (C) STRANDEDNESS: both
      (D) TOPOLOGY: linear (ii) MOLECULE TYPE: DNA (xi) SEQUENCE DESCRIPTION: SEQ ID NO:3:

ACTAGACAAT GTAGAAGAGG CAGAATATGG                30

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:4:

TGTTGCAAGA GCCAACATAA CATGAATAGC                30

(2) INFORMATION FOR SEQ ID NO:5:

(i) SEQUENCE CHARACTERISTICS:
        (A) LENGTH: 39 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:5:

GGGCCCGGAT CCGGTAACAC AATACCACCA AGTTCTGGC      39

(2) INFORMATION FOR SEQ ID NO:6:

(i) SEQUENCE CHARACTERISTICS:
        (A) LENGTH: 40 base pairs
        (B) TYPE: nucleic acid
        (C) STRANDEDNESS: both
        (D) TOPOLOGY: linear (ii) MOLECULE TYPE: DNA (xi) SEQUENCE DESCRIPTION: SEQ ID NO:6:

CCCGGGGGAT CCCTTCCCAC TTTTGTAATT GTTGTATCCC     40

RECOMBINANT FIV GLYCOPROTEIN 160 AND P24 GAG PROTEIN

FIELD OF THE INVENTION

The present invention relates generally to the fields of hematology, immunology and recombinant genetics. The invention specifically relates to recombinant feline immunodeficiency virus glycoprotein 160 envelope protein and fragments thereof, and p24 gag protein and fragments thereof. In another aspect, it relates to the use of the FIV antigens and fragments to induce, in a feline, antibodies to FIV.

DESCRIPTION OF THE BACKGROUND ART

Feline immunodeficiency virus (FIV), formerly called feline T lymphotropic lentivirus (Pederson et al., *Science*, 235:790 (1987)), has been identified in the United States, the United Kingdom (Harbour et al., *Vet Rec*, 122:84 (1988)), Japan (Ishida et al., *Jpn J Vet Sci*, 50:39 (1988)), Australia (Sabine et al., *Aust Vet Practit*, 18:105 (1988)), and New Zealand (Swinney et al., *NZ Vet J*, 37:41 (1989)). The virus appears to be spread by horizontal transmission, predominantly by bite wounds (Yamamoto et al., *Am. J. Vet. Res.*, 8:1246 (1988); Friend et al., *Aust. Vet J.*, 67:237 (1990). FIV has been classified as a member of the subfamily Lentivirinae in the family Retroviridae. This is the family that includes human and simian immunodeficiency viruses, equine infectious anaemia, maedi visna of sheep and caprine-arthritis encephalitis viruses (CAEV).

Cloning and sequencing of FIV has confirmed it to be a lentivirus by its genomic organization and antigenic similarity of its core proteins to those of visna virus and CAEV (Olmsted et al., *Proc. Natl. Acad. Sci. USA*, 86:2448 (1989); Talbott et al., *Proc. Natl. Acad. Sci. USA*, 86:5743 (1989); Dow et al., *Journal Of Acquired Immune Deficiency Syndromes*, 3:658 (1990).

Until the present time, however, very little information has been available regarding the outer shell, or envelope, of the feline immunodeficiency virus. Inasmuch as an elucidation of envelope proteins would be of great value in understanding and modulating the immunological characteristics of FIV, a need has continued to exist for such data.

SUMMARY OF THE INVENTION

Accordingly, the present inventors have succeeded in cloning and expressing novel envelope proteins and protein fragments of FIV, which are useful in the diagnosis and treatment of this immune condition. Specifically, the inventors report the FIV glycoprotein 160 envelope protein, as well as the FIV 0.4 envelope protein, which is an amplified product of the FIV gp160 envelope protein. The inventors also report the novel FIV 1.2 envelope protein that is an amplified product obtained from the region of FIV envelope from position 6996 to 8129.

In addition to the novel envelope proteins and fragments, the inventors have successfully identified p24 gag protein from FIV which is also useful in the diagnosis and treatment of FIV. The inventors have further identified FIV 0.6 which is an amplified product obtained from FIV gag protein.

It is an object of the present invention, then, to provide for a method of diagnosing the infection of a feline by FIV. The present invention thus provides an important advance in the study and therapy of feline immune deficiency syndromes.

The work presented here demonstrates that recom-binant FIV 0.4 envelope protein may be expressed by a transformed cell. The production of recombinant FIV 0.4 envelope protein makes possible new assays and treatments for FIV. It is therefore an object of the present invention to use recombinant proteins from the gp160 envelope protein and the gag protein to develop vaccines in the prevention of FIV infection in cats.

Thus in one embodiment, there is provided according to the invention recombinant functionally active feline immunodeficiency virus 0.4 envelope protein, or a functional or chemical derivative thereof.

In yet another embodiment is provided the FIV gp160 derived 0.4 envelope fragment which is produced by eukaryotic cells. Yet another embodiment of the invention comprises the plasmid pLCBCOFIVO.4. There is also provided according to this invention, methods for producing FIV gp160 derived 0.4 envelope protein, comprising culturing the transformed cell under conditions allowing expression of the gp160 derived 0.4 envelope fragment, and recovering said gp160 derived 0.4 envelope protein.

In yet another embodiment, the present invention provides for an antibody against the FIV envelope protein of the invention.

Further a method of purifying FIV from a sample is provided according to the present invention, comprising contacting said sample with the antibody of the invention, so as to form a complex between said antibody and FIV in said sample, and removing the FIV from said antibody so as to obtain purified FIV.

Moreover, a method of detecting FIV in a sample comprising contacting said sample with the antibody of the invention, wherein said antibody is detectably labeled, so as to form a complex between FIV in said sample and said detectably labeled antibody, and detecting the complexed or uncomplexed detectably labeled antibody.

An additional embodiment of the current invention comprises a pharmaceutical preparation comprising the antibody of the invention. In another embodiment, there is provided a process for the preparation of a pharmaceutical composition useful for inducing the production in a cat of antibodies to FIV, the process comprising admixing an immunologically effective amount of the polypeptide comprising the amino acid sequence of the gp160, gp120 or FIV 0.4 envelope protein together with a pharmaceutically acceptable carrier.

These and other non-limiting embodiments of the present invention will be apparent to those of skill from the following detailed description of the invention.

DESCRIPTION OF THE PREFERRED EMBODIMENTS

Figures 1, 2:
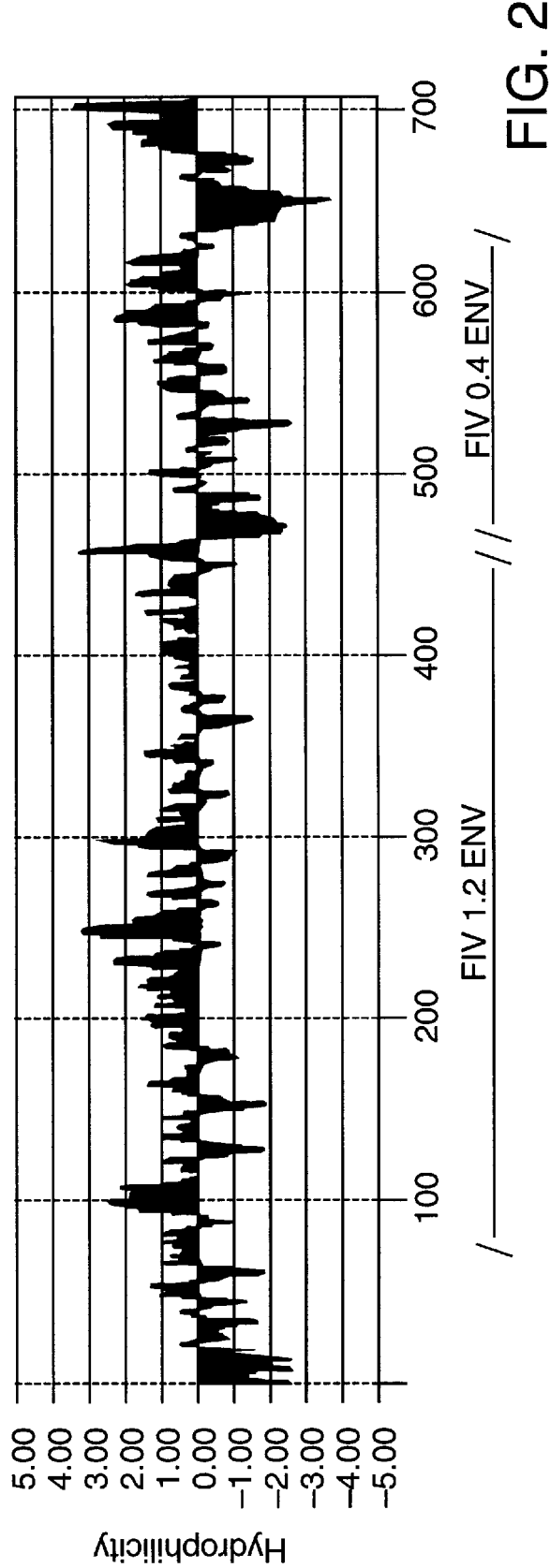
FIG. 1 shows the sequences of the PCR primers. The underlined regions indicate BamHI restriction sites.
FIG. 2 shows the position of the 0.4 amplified product relative to the entire gp 160 envelope protein.
Figure 3:
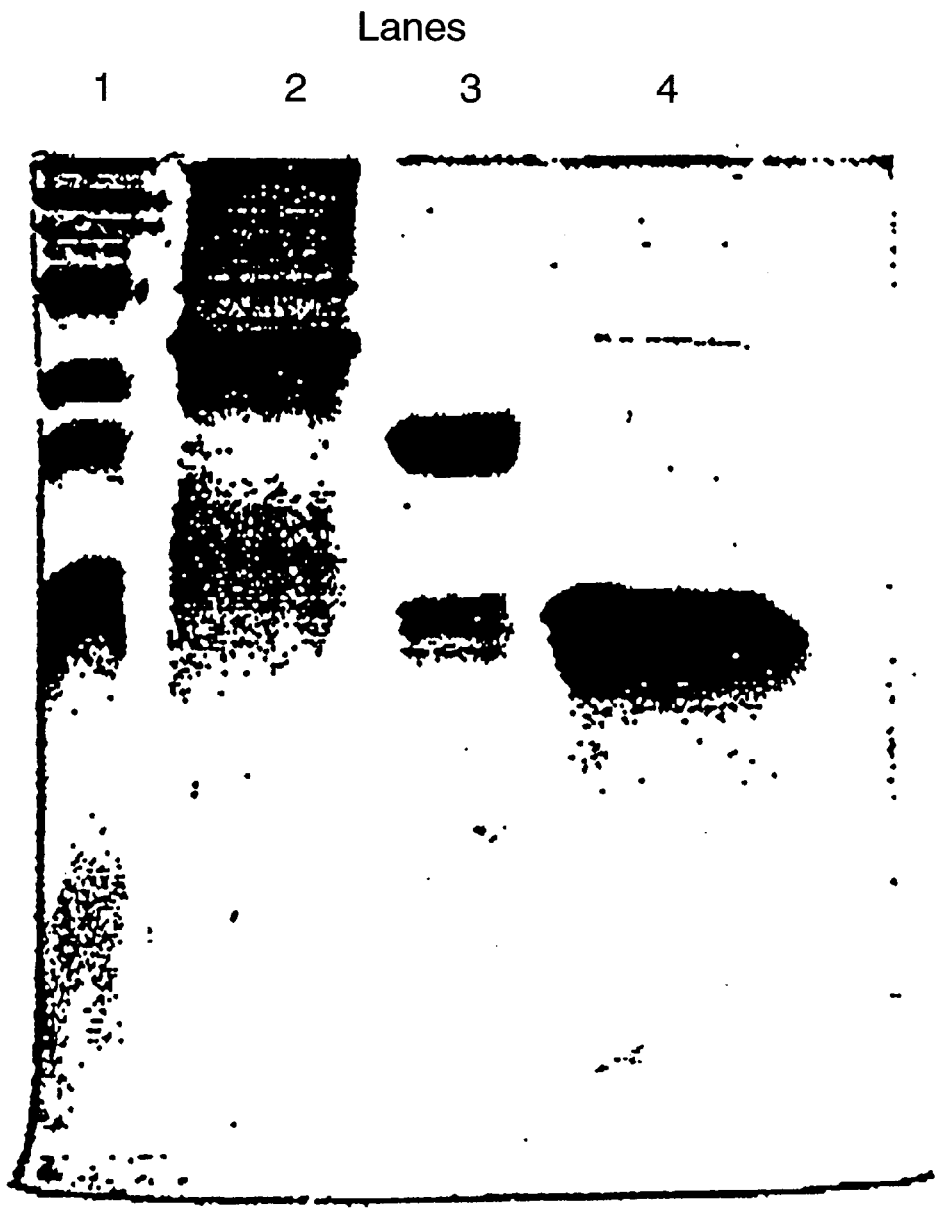
FIG. 3 shows purified recombinant proteins from FIV. Lane 1 contains the molecular weight markers. Lane 2 is a recombinant protein from the gp 120 region of the FIV envelope gene. Lane 3 is a recombinant FIV p24 gag protein. Lane 4 contains the FIV 0.4 envelope diagnostic protein.
Figure 4:
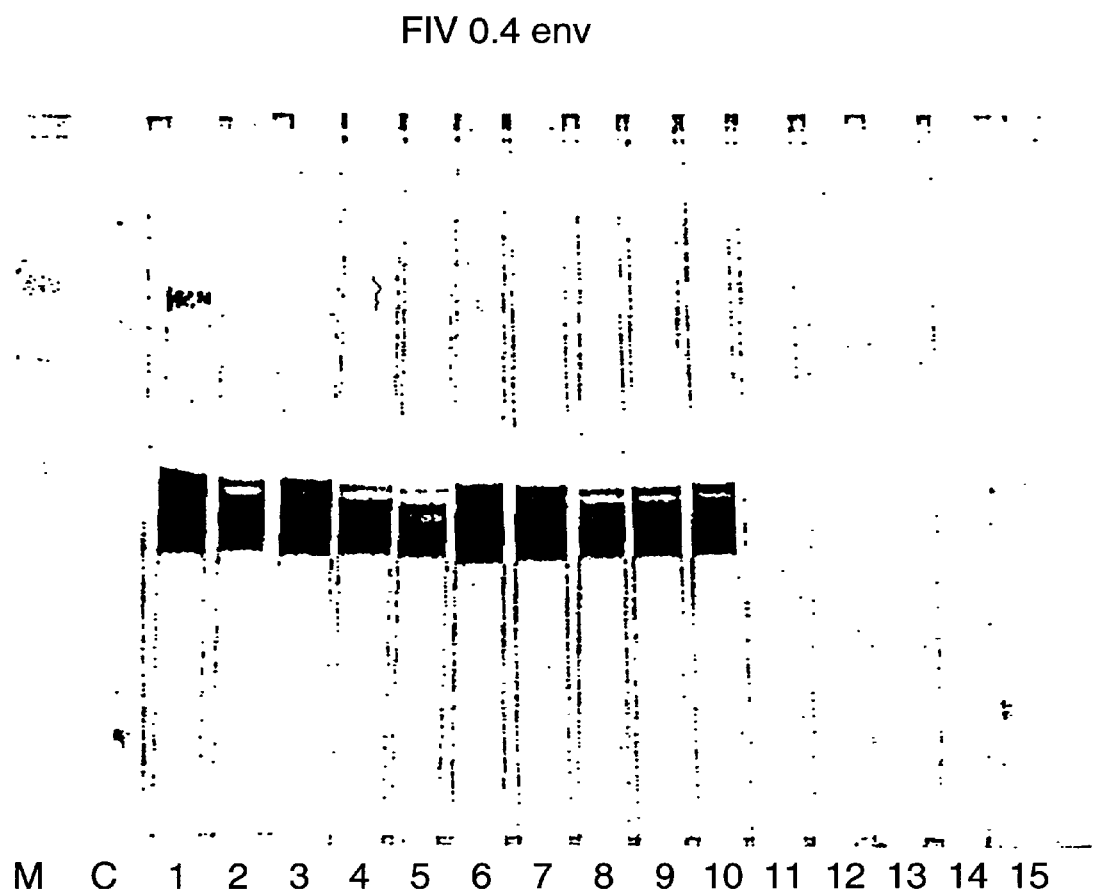
FIG. 4 shows the reactivity of sera from infected cats with the induced FIV 0.4 protein. Lanes 1–10 demonstrate that the protein reacted specifically with sera from FIV-infected cats. Lanes 11–15 are negative controls.

In the following description, reference will be made to various methodologies known to those of skill in the art of molecular biology and immunology. Publications and other materials setting forth such known methodologies to which reference is made are incorporated herein by reference in their entireties as though set forth in full.

Standard reference works setting forth the general principles of recombinant DNA technology include Watson, J. D. et al., *Molecular Bioloqy of the Gene*, Volumes I and II, The Benjamin/Cummings Publishing Company, Inc., publisher, Menlo Park, Calif. (1987); Darnell, J. E. et al., *Molecular Cell Biology*, Scientific American Books, Inc., publisher, New York, N.Y. (1986); Lewin, B. M., *Genes II*, John Wiley & Sons, publishers, New York, N.Y. (1985); Old, R. W., et al., *Principles of Gene Manipulation: An Introduction to Genetic Engineering*, 2d edition, University of California Press, publisher, Berkeley, Calif. (1981); and Sambrook, J., et al., *Molecular Cloning: A Laboratory Manual*, 2nd Ed. Cold Spring Harbor Laboratory, publisher, Cold Spring Harbor, N.Y. (1989).

DEFINITIONS

The term "immunologically effective amount" as used in the invention, is meant to denote the amount of FIV 0.4 envelope protein or FIV gp160 or FIV gp120 envelope protein or FIV 0.6 gag fragment which is necessary to induce production in a cat of antibodies which will bind to FIV epitopes.

By "cloning" is meant the use of in vitro recombination techniques to insert a particular gene or other DNA sequence into a vector molecule. In order to successfully clone a desired gene, it is necessary to employ methods for generating DNA fragments, for joining the fragments to vector molecules, for introducing the composite DNA molecule into a host cell in which it can replicate, and for selecting the clone having the target gene from amongst the recipient host cells.

By "vector" is meant a DNA molecule, derived from a plasmid or bacteriophage, into which fragments of DNA may be inserted or cloned. A vector will contain one or more unique restriction sites, and may be capable of autonomous replication in a defined host or vehicle organism such that the cloned sequence is reproducible. Thus, by "DNA expression vector" is meant any autonomous element capable of replicating in a host independently of the host's chromosome, after additional sequences of DNA have been incorporated into the autonomous element's genome. Such DNA expression vectors include bacterial plasmids and phages.

By "substantially pure" is meant any antigen of the present invention, or any gene encoding any such antigen, which is essentially free of other antigens or genes, respectively, or of other contaminants with which it might normally be found in nature, and as such exists in a form not found in nature. By "functional derivative" is meant the "fragments," "variants," "analogues," or "chemical derivatives" of a molecule. A "fragment" of a molecule, such as any of the DNA sequences of the present invention, is meant to refer to any nucleotide subset of the molecule. A "variant" of such molecule is meant to refer to a naturally occurring molecule substantially similar to either the entire molecule, or a fragment thereof. An "analog" of a molecule is meant to refer to a non-natural molecule substantially similar to either the entire molecule or a fragment thereof.

A molecule is said to be "substantially similar" to another molecule if the sequence of amino acids in both molecules is substantially the same. Substantially similar amino acid molecules will possess a similar biological activity. Thus, provided that two molecules possess a similar activity, they are considered variants as that term is used herein even if one of the molecules contains additional amino acid residues not found in the other, or if the sequence of amino acid residues is not identical. As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed, for example, in *Remington's Pharmaceutical Sciences*, 16th ed., Mack Publishing Co., Easton, Pa. (1980).

Similarly, a "functional derivative" of a gene of the FIV 0.4 envelope protein, FIV 1.2 envelope protein or FIV 0.6 fragment of the present invention is meant to include "fragments," "variants," or "analogues" of the gene, which may be "substantially similar" in nucleotide sequence, and which encode a molecule possessing similar activity to the FIV 0.4 peptide.

Thus, as used herein, FIV 0.4 envelope protein, FIV 1.2 envelope protein and FIV 0.6 are also meant to include any functional derivative, fragments, variants, analogues, chemical derivatives which may be substantially similar to the peptides FIV 0.4, FIV 1.2 and FIV 0.6 and which possess similar activity.

A DNA sequence encoding the FIV 0.4 envelope protein, FIV 1.2 envelope protein or FIV 0.6 fragment of the present invention, or its functional derivatives, may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Maniatis, T., et al., supra, and are well known in the art.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression. The precise nature of the regulatory regions needed for gene expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Such regions will normally include those 5'-non-coding sequences involved with initiation of transcription and translation, such as the TATA box, capping sequence, CAAT sequence, and the like.

If desired, the non-coding region 3' to the gene sequence coding for the protein may be obtained by the above-described methods. This region may be retained for its transcriptional termination regulatory sequences, such as termination and polyadenylation. Thus, by retaining the 3'-region naturally contiguous to the DNA sequence coding for the protein, the transcriptional termination signals may be provided. Where the transcriptional termination signals are not satisfactorily functional in the expression host cell, then a 3' region functional in the host cell may be substituted.

Two DNA sequences (such as a promoter region sequence and a FIV 0.4 envelope protein encoding sequence) are said to be operably linked if the nature of the linkage between the two DNA sequences does not (1) result in the introduction of a frame-shift mutation, (2) interfere with the ability of the promoter region sequence to direct the transcription of the FIV 0.4 envelope protein gene sequence, or (3) interfere with the ability of the FIV 0.4 envelope gene sequence to be transcribed by the promoter region sequence. A promoter region would be operably linked to a DNA sequence if the promoter were capable of effecting transcription of that DNA sequence. Thus, to express the protein, transcriptional and translational signals recognized by an appropriate host are necessary.

The present invention encompasses the expression of the FIV 0.4 envelope protein, FIV 1.2 envelope protein, and FIV 0.6 gag fragment (or a functional derivative thereof) in either prokaryotic or eukaryotic cells, although prokaryotic expression is preferred.

Antibodies according to the present invention may be prepared by any of a variety of methods. For example, cells expressing the FIV 0.4 envelope protein, or a functional derivative thereof, can be administered to an animal in order to induce the production of sera containing polyclonal antibodies that are capable of binding the chimera.

In a preferred method, antibodies according to the present invention are monoclonal antibodies. Such monoclonal antibodies can be prepared using hybridoma technology (Kohler et al., *Nature* 256:495 (1975); Kohler et al., *Eur. J. Immunol.* 6:511 (1976); Kohler et al., *Eur. J. Immunol.* 6:292 (1976); Hammerling et al., In: *Monoclonal Antibodies and T-Cell Hybridomas*, Elsevier, N.Y., pp. 563–681 (1981)). In general, such procedures involve immunizing an animal with the FIV 0.4 envelope protein antigen. The splenocytes of such animals are extracted and fused with a suitable myeloma cell line. Any suitable myeloma cell line may be employed in accordance with the present invention. After fusion, the resulting hybridoma cells are selectively maintained in HAT medium, and then cloned by limiting dilution as described by Wands, J.R., et al. (*Gastroenterology* 80:225–232 (1981). The hybridoma cells obtained through such a selection are then assayed to identify clones which secrete antibodies capable of binding the FIV 0.4 envelope protein antigen.

Antibodies according to the present invention also may be polyclonal, or, preferably, region specific polyclonal antibodies.

Antibodies against the FIV 0.4 envelope protein, the FIV 1.2 envelope protein and the FIV gag 0.6 protein according to the present invention are well suited for use in standard immunodiagnostic assays known in the art, including such immunometric or "sandwich" assays as the forward sandwich, reverse sandwich, and simultaneous sandwich assays. The antibodies may be used in any number of combinations as may be determined by those of skill without undue experimentation to effect immunoassays of acceptable specificity, sensitivity, and accuracy for the receptor antigen or equivalents thereof.

Standard reference works setting forth general principles of immunology include Roitt, I., *Essential Immunology*, Sixth Ed., Blackwell Scientific Publications, Publisher, Oxford (1988); Kimball, J. W., *Introduction to Immunology*, Second Ed., Macmillan Publishing Co., Publisher, New York (1986); Roitt, I., et al., *Immunology*, Gower Medical Publishing Ltd., Publisher, London, (1985); Campbell, A., "Monoclonal Antibody Technology," in, Burdon, R., et al., eds., *Laboratory Techniques in Biochemistry and Molecular Biology*, Volume 13, Elsevier, Publisher, Amsterdam (1984); Klein, J., *Immunology: The Science of Self-Nonself Discrimination*, John Wiley & Sons, Publisher, New York (1982); and Kennett, R., et al., eds., *Monoclonal Antibodies, Hybridoma: A New Dimension in Biological Analyses*, Plenum Press, Publisher, New York (1980).

By "detecting" it is intended to include determining the presence or absence of a substance or quantifying the amount of a substance. The term thus refers to the use of the materials, compositions, and methods of the present invention for qualitative and quantitative determinations.

The isolation of other hybridomas secreting monoclonal antibodies of the same specificity as those described herein can be accomplished by the technique of anti-idiotypic screening. Potocmjak, et al., *Science* 215:1637 (1982). Briefly, an anti-idiotypic antibody is an antibody which recognizes unique determinants present on the antibody produced by the clone of interest. The anti-idiotypic antibody is prepared by immunizing an animal of the same strain used as the source of the monoclonal antibody with the monoclonal antibody of interest. The immunized animal will recognize and respond to the idiotypic determinants of the immunizing antibody by producing antibody to these idiotypic determinants (anti-idiotypic antibody).

For replication, the hybrid cells may be cultivated both in vitro and in vivo. High in vivo production makes this the presently preferred method of culture. Briefly, cells from the individual hybrid strains are injected intraperitoneally into pristine-primed BALB/c mice to produce ascites fluid containing high concentrations of the desired monoclonal antibodies. Monoclonal antibodies of isotype IgM or IgG may be purified from cultured supernatants using column chromatography methods well known to those of skill in the art.

Antibodies according to the present invention are particularly suited for use in immunoassays wherein they may be utilized in liquid phase or bound to a solid phase carrier. In addition, the antibodies in these immunoassays can be detectably labeled in various ways.

There are many different labels and methods of labeling known in the art. Examples of the types of labels which can be used in the present invention include, but are not limited to, enzymes, radioisotopes, fluorescent compounds, chemiluminescent compounds, bioluminescent compounds and metal chelates. Those of ordinary skill in the art will know of other suitable labels for binding to antibodies, or will be able to ascertain the same by the use of routine experimentation. Furthermore, the binding of these labels to antibodies can be accomplished using standard techniques commonly known to those of ordinary skill in the art.

One of the ways in which antibodies according to the present invention can be detectably labeled is by linking the antibody to an enzyme. This enzyme, in turn, when later exposed to its substrate, will react with the substrate in such a manner as to produce a chemical moiety which can be detected as, for example, by spectrophotometric or fluorometric means. Examples of enzymes which can be used to detectably label antibodies include malate dehydrogenase, staphylococcal nuclease, delta-V-steroid isomerase, yeast alcohol dehydrogenase, α-glycerophosphate dehydrogenase, triose phosphate isomerase, biotin-avidin peroxidase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase.

The presence of detectably labeled antibodies also can be detected by labeling the antibodies with a radioactive isotope which then can be determined by such means as the use of a gamma counter or a scintillation counter. Isotopes which are particularly useful for the purpose of the present invention are $^{3}$H, $^{125}$I, $^{32}$P, $^{35}$S, $^{14}$C, $^{51}$Cr, $^{36}$Cl, $^{57}$Co, $^{58}$Co, $^{59}$Fe and $^{75}$Se.

It is also possible to detect the binding of detectably labeled antibodies by labeling the antibodies with a fluorescent compound. When a fluorescently labeled antibody is exposed to light of the proper wave length, its presence then can be detected due to the fluorescence of the dye. Among the most commonly used fluorescent labeling compounds are fluorescein, isothiocyanate, rhodamine, phycoerythrin, phycocyanin, allophycocyanin, o-phthaldehyde and fluorescamine.

The antibodies of the invention also can be detectably labeled using fluorescent emitting metals such as $^{152}$Eu, or others of the lanthanide series. These metals can be attached to the antibody molecule using such metal chelating groups as diethylene-triaminepentaacetic acid (DTPA) or ethylenediamine-tetraacetic acid (EDTA).

Antibodies also can be detectably labeled by coupling them to a chemiluminescent compound. The presence of the chemiluminescent-tagged antibody is then determined by detecting the presence of luminescence that arises during the course of the chemical reaction. Examples of particularly useful chemiluminescent labeling compounds are luminol, isoluminol, theromatic acridinium ester, imidazole, acridinium salts, oxalate ester, and dioxetane.

Likewise, a bioluminescent compound may be used to label the antibodies according to the present invention. Bioluminescence is a type of chemiluminescence found in biological systems in which a catalytic protein increases the efficiency of the chemiluminescent reaction. The presence of a bioluminescent antibody is determined by detecting the presence of luminescence. Important bioluminescent compounds for purposes of labeling include luciferin, luciferase and aequorin.

The antibodies and substantially purified antigen of the present invention are ideally suited for the preparation of a kit. Such a kit may comprise a carrier means being compartmentalized to receive in close confinement therewith one or more container means such as vials, tubes and the like, each of said container means comprising the separate elements of the assay to be used.

The types of assays which can be incorporated in kit form are many, and include, for example, competitive and non-competitive assays. Typical examples of assays which can utilize the antibodies of the invention are radioimmunoassays (RIA), enzyme immunoassays (EIA), enzyme-linked immunosorbent assays (ELISA), and immunometric, or sandwich, immunoassays.

By the term "immunometric assay" or "sandwich immunoassay," it is meant to include simultaneous sandwich, forward sandwich and reverse sandwich immunoassays. These terms are well understood by those skilled in the art. Those of skill will also appreciate that antibodies according to the present invention will be useful in other variations and forms of assays which are presently known or which may be developed in the future. These are intended to be included within the scope of the present invention.

In the preferred mode for performing the assays it is important that certain "blockers" be present in the incubation medium (usually added with the labeled soluble antibody). The "blockers" are added to assure that non-specific proteins, protease, or feline antibodies to mouse immunoglobulins present in the experimental sample do not cross-link or destroy the antibodies on the solid phase support, or the radiolabeled indicator antibody, to yield false positive or false negative results. The selection of "blockers" therefore adds substantially to the specificity of the assays described in the present invention.

It has been found that a number of nonrelevant (i.e. nonspecific) antibodies of the same class or subclass (isotype) as those used in the assays (e.g. $IgG_1$, $IgG_{2a}$, IgM, etc.) can be used as "blockers." The concentration of the "blockers" (normally 1–100 mg/$\mu$l) is important, in order to maintain the proper sensitivity yet inhibit any unwanted interference by mutually occurring cross reactive proteins in feline serum. In addition, the buffer system containing the "blockers" needs to be optimized. Preferred buffers are those based on weak organic acids, such as imidazole, HEPPS, MOPS, TES, ADA, ACES, HEPES, PIPES, TRIS, and the like, at physiological pH ranges. Somewhat less preferred buffers are inorganic buffers such as phosphate, borate or carbonate. Finally, known protease inhibitors should be added (normally at 0.01–10 $\mu$g/ml) to the buffer which contains the "blockers."

There are many solid phase immunoadsorbents which have been employed and which can be used in the present invention. Well known immunoadsorbents include glass, polystyrene, polypropylene, dextran, nylon and other materials, in the form of tubes, beads, and microtiter plates formed from or coated with such materials, and the like. The immobilized antibodies can be either covalently or physically bound to the solid phase immunoadsorbent, by techniques such as covalent bonding via an amide or ester linkage, or by adsorption. Those skilled in the art will know many other suitable solid phase immunoadsorbents and methods for immobilizing antibodies thereon, or will be able to ascertain such, using no more than routine experimentation.

For in vivo, in vitro or in situ diagnosis, labels such as radionuclides may be bound to antibodies according to the present invention either directly or by using an intermediary functional group. An intermediary group which is often used to bind radioisotopes which exist as metallic cations to antibodies is diethylenetriaminepentaacetic acid (DTPA). Typical examples of metallic cations which are bound in this manner are: $^{99m}$Tc, $^{123}$I, $^{111}$IN, 131I, $^{97}$Ru, $^{67}$Cu, $^{67}$Ga and $^{68}$Ga. The antibodies of the invention can also be labeled with non-radioactive isotopes for purposes of diagnosis. Elements which are particularly useful in this manner are $^{157}$Gd, $^{55}$Mn, $^{162}$Dy, $^{52}$Cr and $^{56}$Fe.

The antigens of the invention may be isolated in substantially pure form employing antibodies according to the present invention. Thus, an embodiment of the present invention provides for substantially pure FIV 0.4 envelope protein, FIV 1.2 envelope protein, and FIV 0.6 gag protein, said antigens characterized in they are recognized by and bind to antibodies according to the present invention. In another embodiment, the present invention provides a method of isolating or purifying the FIV 0.4 envelope protein, FIV 1.2 envelope protein and FIV 0.6 gag protein antigens, by forming a complex of said antigen with one or more antibodies directed against the FIV 0.4 envelope protein, FIV 1.2 envelope protein and FIV 0.6 gag protein respectively.

The substantially pure antigens of the present invention may in turn be used to detect or measure antibodies to either FIV 0.4 envelope protein, FIV 1.2 envelope protein or FIV 0.6 gag protein in a sample, such as serum or urine. Thus, one embodiment of the present invention comprises a method of detecting the presence or amount of antibody to the FIV 0.4 envelope protein antigen in a sample, comprising contacting said sample containing said antibody to the FIV 0.4 envelope antigen with detectably labeled FIV 0.4 envelope protein, and detecting said label. It will be appreciated that immunoreactive fractions and immunoreactive analogues of the fragment also may be used. By the term "immunoreactive fraction" is intended any portion of the FIV 0.4 envelope protein antigen which demonstrates an equivalent immune response to an antibody directed against the receptor chimera. By the term "immunoreactive analogue" is intended a protein which differs from the receptor fragment by one or more amino acids, but which demonstrates an equivalent immunoresponse to an antibody of the invention.

The pharmaceutical compositions of the invention may be administered to any animal which may experience the beneficial effects of the compounds of the invention. Foremost among such animals are felines, although the invention is not intended to be so limited.

The manner and method of carrying out the present invention may be more fully understood by those of skill by reference to the following examples, which examples are not intended in any manner to limit the scope of the present invention or of the claims directed thereto.

EXAMPLE I

Construction of FIV Envelope and GAG Expressing Clones

Genomic DNA was extracted from FIV-infected feline peripheral blood leukocytes. FIV published sequence data (Talbott et al., *Proc. Natl. Acad. Sci*., 86: 5743 (1989)) was used to create oligonucleotide primers for polymerase chain reaction. The primers amplify the region of FIV envelope from position 8178 to 8576 and also contain BamBI restriction sites with GC-rich clamps at each 5' end to simplify cloning. FIG. 1 details the sequence of these primers.

Oligonucleotides used as primers were synthesized by the phosphoroamidite method using an automated DNA synthesizer (Milligen). Prior to amplification, genomic DNA was heat denatured by boiling for five minutes and then was added to the PCR reaction mixes at a final concentration of 1 ug per reaction. The PCR reaction mix contained final concentrations of each of the following: 50 mM KCl, 10 mM Tris HCl, pH 8.3 at room temperature, 0.01% gelatin, 1.5 mM MgCl2, 320 uM of each DATP, dTTP, dCTP, and dGTP and 0.77 uM of each primer. The PCR reactions were conducted in the Techne Programmable Driblock PHC-1 with the following thermal profile: 95 degrees celsius for 1 minute, 37 degrees celsius for 1 minute, and 72 degrees celsius for 3 minutes for 35 cycles with a final extension at 72 degrees for 5 minutes.

The position of the 0.4 kb amplified product relative to the entire FIV gp 160 envelope protein is illustrated in FIG. 2. The 0.4 kb amplified product was digested with restriction enzyme BamBI which only cuts the linker region of each primer (refer to FIG. 1). The BamBI cut PCR product was purified and cloned into BamHlI restricted expression vector pLCBCO to generate clone pLCBCOFIVO.4.

Plasmid pLCBCO is an *E. coli* expression vector that makes use of the bacteriophage lambda pL promoter. PLCBCO is similar to pJL6 described completely in Beltz et al., U.S. Pat. No. 4,753,873, incorporated herein by reference.

Purification of FIV Recombinant Proteins

*E. coli* cells were fermented at 32 degrees C. to an O.D. 550 of 10.0. The expression of the FIV 0.4 diagnostic protein was induced by temperature shift to 42 degree C. for 2 hours. The cells were then harvested by centrifugation at 4000×g for 20 minutes and lysed by enzymatic digestion with 0.5 mg/ml lysozyme in 50 mM Tris HCl, pH 7.5, containing aprotinin (25 $\mu$g/ml), 2mM PMSF, 25 ug/ml DNase I and 1% Triton-X 100 for 30 minutes with constant stirring. At the end of digestion, the mixture was centrifuged at 12,000×g for 30 minutes and the resulting pellet was redigested with lysozyme using the same conditions as described above. This was followed by one wash with 0.5% sodium deoxycholate in 50 mM sodium carbonate, pH 10.0. The antigen in the pellet was then solubilized with 0.5% zwittergen 3–14 in the same carbonate buffer. The antigen in the zwittergen supernatant was precipitate by adjusting pH of the solution to 6.0, resolubilized in 6M guanidine HCl, 50 mM borate, pH 9.0, 0.2% beta-mercaptoethanol, alkylated with iodoacetic acid at 1.2 fold molar excess over beta-mercaptoethanol and finally dialyzed against 8M urea, 50 mM borate pH 9.0.

The alkylated dialyzed antigen was then citraconylated by the addition of a 50 fold molar excess of citraconic anhydride (over protein amino groups). After citraconylation, the antigen solution was dialyzed exhaustively against 50 mM sodium borate, pH 9.0 and loaded onto a DEAE-TSK column equilibrated with the same buffer. The DEAE-TSK column was then developed with a linear gradient of 0–1M NaCl to obtain purified recombinant antigen.

FIG. 3 shows the purified recombinant proteins. Lane 1 contains molecular weight markers. Lane 2 is the FIV 1.2 envelope gene. Lane 3 is the FIV 0.6 p24 gag protein and lane 4 is the FIV 0.4 envelope protein.

Use of the FIV 0.4 Protein in Detection of FIV Infection in Cats

In the use of the FIV 0.4 envelope protein for diagnosis of FIV infection, the purified protein was electrophoresed through acrylamide gels and the protein transferred by Western blot to nitrocellulose membranes. Individual strips containing FIV 0.4 protein were reacted with sera from 10 FIV infected cats and with 5 negative controls. The results are shown in FIG. 4.

EXAMPLE 2

Construction of an FIV gag Expressing Clone (FIV 0.6)

The same genomic DNA that was used for PCR in Example 1 was also used in this example. FIV published sequence data (Talbott et al., *Proc. Natl. Acad. Sci*. 86:5743 (1989)) was used to create oligonucleotide primers for PCR. These primers amplify a region of FIV gag from position 1050 to 1644 and also contain BamBI restriction sites and GC-rich clamps. The sequences of these primers are:

Primer 3: 5' amplimer, position 1050 to 1069 5'CCGGGGATCCGGAGTACCACAATATGTAGC-3' [SEQ ID NO:1]

Primer 4: 3' amplimer, reverse compliment of positions 1625 to 1644 5'-GGCCGGATCCCTTCTAGGGTACTTTCTGGC-3'[SEQ ID NO:2]

The oligonucleotide primers were synthesized and PCR amplification was conducted in the same manner as in Example 1. The resulting 0.6 kb fragment was digested with BamBI, which only cuts in the linker region of each primer. The BamBI restricted PCR product was purified and cloned into BamBI restricted expression vector pLCBC1 to generate the clone pLCBClFIVO.6.

Plasmid pLCBC1 differs from pLBCB0 by the addition of a single base pair just prior to the BamBI cloning site. pLCBC1 was used in this case over pLCBC0 to allow for proper reading frame alignment. pLCBC1 is also described in Beltz et al., U.S. Pat. No. 4,753,873, incorporated herein by reference.

The resulting plasmid was transferred into *E. coli* host MZ-1 for expression as in Example 1.

EXAMPLE 3

Construction of an FIV Envelope Expressing Clone (FIV 1.2)

The same genomic DNA that was used for PCR in Examples 1 and 2 was also used in this example. FIV published sequence data (Talbott et al., *Proc. Natl. Acad. Sci.* 86:5743 (1989)) was used to create oligonucleotide primers for PCR. These primers amplify a region of FIV envelope from position 6996 to 8129, but do not contain BamBI restriction sites for GC-rich clamps. The sequences of these primers are:

Primer 5: 5' amplimer, position 6996 to 7025 5'ACTAGACAATGTAGAAGAGGCAGAATATGG-3'[SEQ ID NO:3]

Primer 6: 3' amplimer, reverse compliment of positions 8101 to 8129 5'-TGTTGCAAGAGCCAACATAACATGAATAGC-3'[SEQ ID NO:4]

The oligonucleotide primers were synthesized and PCR amplification was conducted in the same manner as in Examples 1 and 2. The resulting 1.2 kb fragment was ligated to BamBI linkers (New England Biolabs #1003). The resulting BamBI-linked PCR product was digested with BamBI, purified and cloned into BamBI restricted expression vector pLCBC2 to generate the clone pLCBC2FIV1.2.

Plasmid pLCBC2 differs from pLCBC0 by the addition of two base pairs just prior to the BamBI cloning site. PLCBC2 was used in this case over pLCBC0 to allow for proper reading frame alignment. PLCBC2 is also described in Beltz et al., U.S. Pat. No. 4,753,873, incorporated herein by reference.

The resulting plasmid was transferred into *E. coli* host MZ-1 for expression as in Examples 1 and 2.

From the foregoing, those of skill will appreciate that, although specific embodiments of the invention have been described herein for illustrative purposes, various modifications may be made without deviating from the spirit and scope of the invention. Accordingly, the invention is not limited except as by the appended claims.

We claim:

1. A substantially pure recombinant FIV 0.4 envelope protein obtained from cells infected with FIV.

2. The substantially purified recombinant FIV 0.4 envelope protein of claim 1 wherein said FIV is of Bangstom strain.

3. The FIV envelope protein of claim 1 or 2 produced by *E. coli*.

4. The FIV envelope protein of claim 1 or 2 produced from *E. coli* strain MZ-1.

5. A plasmid comprising a DNA sequence coding for a FIV 0.4 envelope protein.

6. A plasmid comprising a DNA sequence coding for a FIV gp160-containing protein.

7. A plasmid comprising a DNA sequence coding for the FIV 0.4 envelope protein of Bangstom strain.

8. A eukaryotic cell transformed with the plasmid of claim 5 or 7.

9. A method of producing FIV 0.4 envelope protein, comprising culturing the transformed cell of claim 8 under conditions allowing expression of FIV 0.4 envelope protein, and recovering said protein.

10. A method as claimed in claim 9, wherein said DNA sequence is derived from FIV Bangstom strain.

11. A process for the preparation of a pharmaceutical composition useful for inducing the production in a cat of antibodies to FIV, the process comprising admixing an immunologically effective amount of the polypeptide comprising the amino acid sequence of the FIV 0.4 envelope protein together with a pharmacologically acceptable carrier.

12. A pharmaceutical composition for the prevention of FIV infection comprising the FIV envelope protein of claim 1 or 2.

13. A pharmaceutical composition for the prevention of FIV infection comprising the FIV envelope protein of claim 3.

14. A pharmaceutical composition for the prevention of FIV infection comprising the FIV envelope protein of claim 4.

15. The use of the pharmaceutical composition of claim 12, in the preparation of a composition for immunizing a cat against FIV.

16. The use of the pharmaceutical composition of claim 13, in the preparation of a composition for immunizing a cat against FIV.

17. The use of the pharmaceutical composition of claim 14, in the preparation of a composition for immunizing a cat against FIV.

18. A kit for detecting FIV antibodies in a sample comprising a carrier being compartmentalized to receive one or more container means in close confinement therein, a first container means comprising a peptide fragment according to any one of claims 1 or 2 immobilized on a solid phase immunoadsorbent and a second container means containing detectably labeled anti-antibody to FIV antibodies.

* * * * *